United States Patent [19]

Taylor

[11] 4,109,837

[45] Aug. 29, 1978

[54] LIQUID SAMPLING DEVICE

[75] Inventor: Glenn N. Taylor, Cary, Ill.

[73] Assignee: The Kendall Company, Boston, Mass.

[21] Appl. No.: 753,112

[22] Filed: Dec. 22, 1976

[51] Int. Cl.² .................... B65D 47/22; F16K 31/14
[52] U.S. Cl. .................................... 222/556; 251/308
[58] Field of Search .................... 251/308, 305, 306; 73/422 R; 222/556; 128/274, 275, 295, 2 F; 150/1

[56] References Cited

U.S. PATENT DOCUMENTS

| 2,772,850 | 12/1956 | Eaton | 251/306 |
| 2,930,574 | 3/1960 | Sebardt | 251/306 X |
| 3,127,904 | 4/1964 | Stillwagon | 251/308 X |
| 3,215,400 | 11/1965 | Muller | 251/308 X |
| 3,415,299 | 12/1968 | Hinman, Jr. et al. | 150/1 X |
| 4,008,877 | 2/1977 | Yasuoka et al. | 251/308 X |

Primary Examiner—Joseph F. Peters, Jr.
Assistant Examiner—Norman L. Stack, Jr.
Attorney, Agent, or Firm—Powell L. Sprunger

[57] ABSTRACT

A liquid sampling device having a tubular section of flexible material having a wall defining a lumen for passage of liquid, and a rigid valve member positioned in the lumen and having a sealing surface for engaging against an inner surface of the tubular section and preventing passage of liquid through the lumen. The tubular section is pressed against the valve member to deform the wall of the tubular section and permit passage of a liquid sample between the valve member and tubular section. The valve member is rotated to a position with at least a portion of the sealing surface of the valve member spaced from the inner surface of the tubular section to permit passage of liquid between the valve member and tubular section.

13 Claims, 9 Drawing Figures

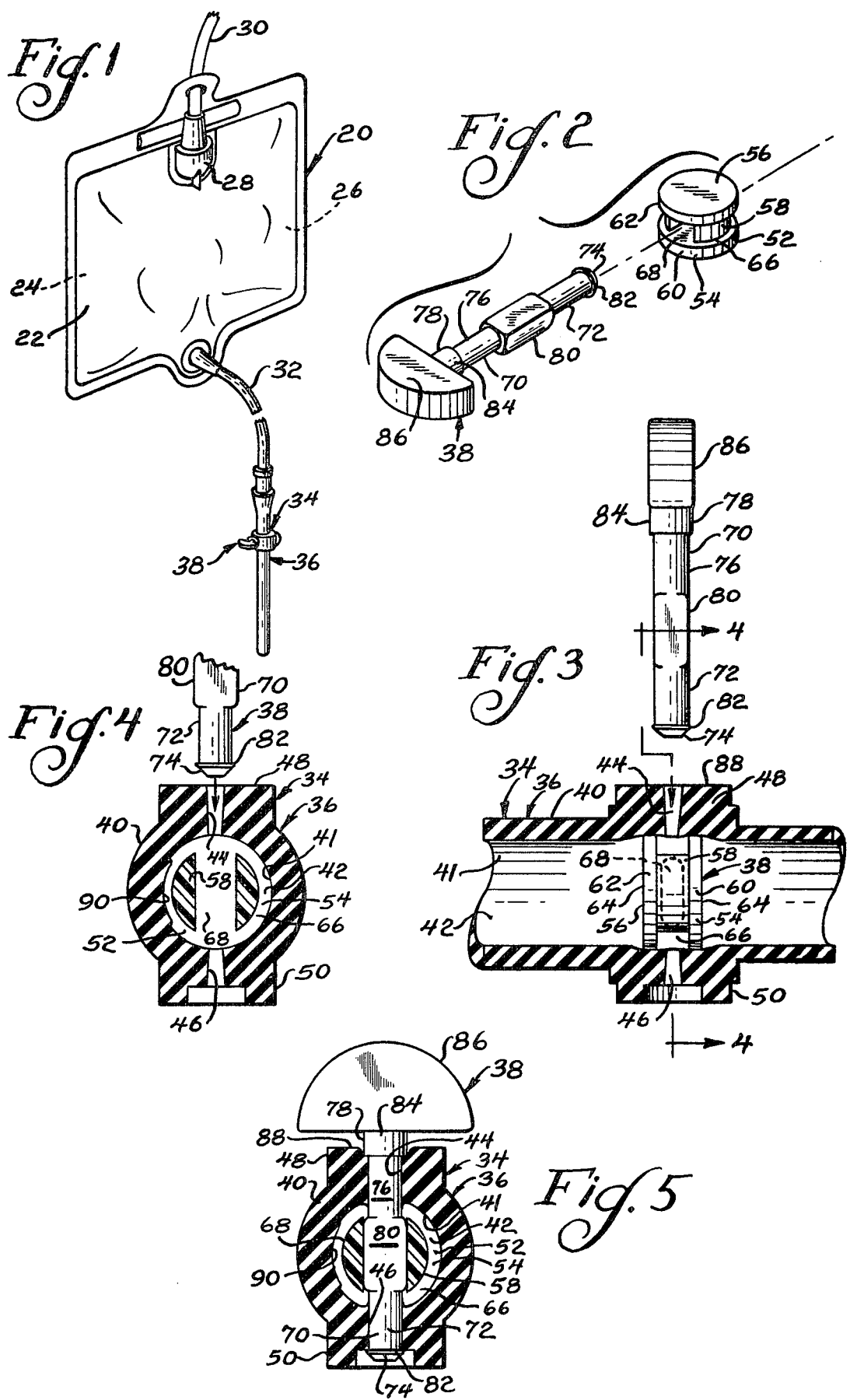

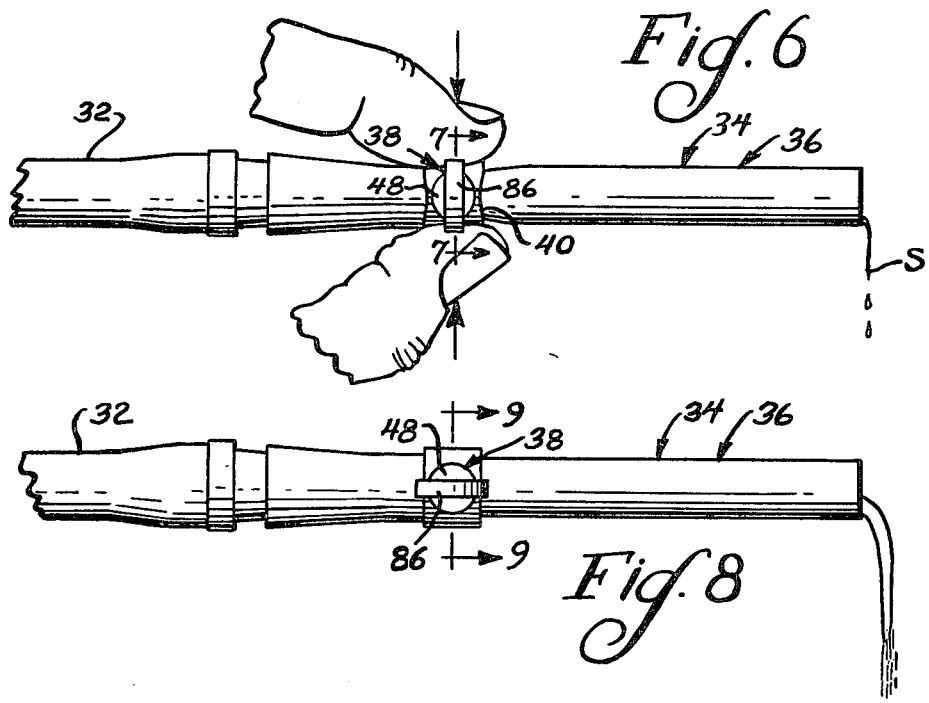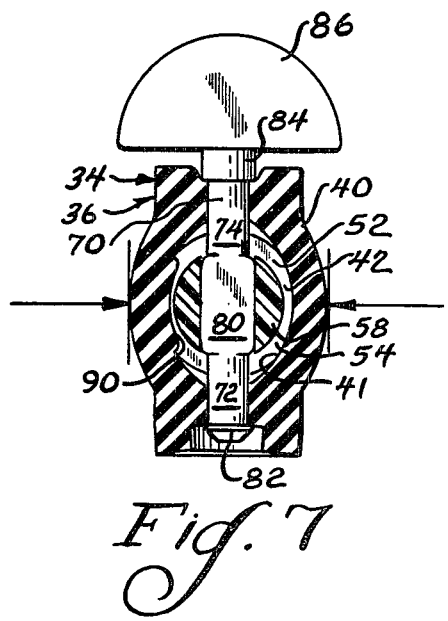

LIQUID SAMPLING DEVICE

BACKGROUND OF THE INVENTION

The present invention relates to liquid flow control devices, and more particularly to such devices for obtaining a liquid sample.

In the past, drainage bags have been used to collect urine from a patient during catheterization. According to standard procedures, a catheter is positioned in the urethra of the patient, and urine drains through the catheter and a drainage tube, which is connected to the catheter, into a chamber in the bag for collection therein. Although such bags may satisfactorily collect the urine, it may be necessary to periodically obtain a small urine sample for purposes of analysis, and the prior art bags have rendered such a sampling procedure relatively difficult. For example, such bags have been commonly provided with a drain tube having a clamp or valve which is designed primarily to drain all of the collected urine from the bag through the drain tube. When it is desired to obtain a sample, a suitable receptacle is positioned beneath the drain tube and the clamp or valve is opened. However, prior clamps and valves used for this purpose are difficult to manipulate with one hand, and when opened, permit passage of an amount of liquid which is excessive for sampling purposes. Thus, it is desirable that a relatively small quantity of urine sample may be obtained during catheterization, while also permitting rapid drainage of the bag when catheterization has been completed.

SUMMARY OF THE INVENTION

A principal feature of the present invention is the provision of a liquid sampling device which permits selective passage of sampling or larger liquid quantities through the device.

The sampling device of the present invention comprises, a tubular section of flexible material having a wall defining a lumen for passage of the liquid. The device has a flow control element comprising, a rigid valve member rotatably positioned in the lumen of the tubular section, with the valve member having a width slightly greater than the internal dimensions of the surrounding tubular section and defining a peripheral surface for sealing against an internal surface of the wall. The valve member has a thickness less than the internal dimensions of the surrounding tubular section in at least one location. The control element has a handle member located outside the tubular section, and a stem extending through the wall of the tubular section and connecting the valve member and handle member.

A feature of the present invention is that the valve member may be located at a first rotational position in the tubular section with the sealing surface of the valve member engaging against the inner surface of the tubular section.

Thus, a feature of the invention is that the valve member closes the lumen and prevents passage of liquid through the tubular section when the valve member is located at the first rotational position.

Another feature of the present invention is that the flexible tubular section may be pressed to deform the wall and permit a relatively small sample of liquid to pass between the valve member and the inner surface of the tubular section.

Yet another feature of the invention is that the valve member may be rotated by the handle member to a second rotational position with at least a portion of the sealing surface spaced from the inner surface of the sampling section.

A feature of the invention is that the valve member permits relative rapid passage of liquid between the valve member and the tubular section when the valve member is located at the second rotational position.

Accordingly, a feature of the invention is that the device may be used to prevent passage of liquid and selectively permit passage of sampling and larger liquid quantities.

Another feature of the invention is that the liquid sample may be obtained in a simplified manner by merely pressing against the tubular section.

Further features will become more fully apparent in the following description of the embodiments of this invention and from the appended claims.

DESCRIPTION OF THE DRAWINGS

In the drawings:

FIG. 1 is a fragmentary perspective view showing a liquid drainage bag and a liquid sampling device of the present invention connected to a lower portion of the drainage bag;

FIG. 2 is an exploded perspective view of a flow control element for the liquid sampling device of the present invention;

FIG. 3 is a fragmentary elevational view, taken partly in section, of a partially assembled sampling device of the present invention;

FIG. 4 is a fragmentary view taken partly in section and being taken substantially as indicated along the line 4—4 of FIG. 3;

FIG. 5 is a view taken partly in section and showing the assembled sampling device of FIG. 4;

FIG. 6 is a fragmentary elevational view of the sampling device while being used to obtain a liquid sample;

FIG. 7 is a view taken partly in section and being taken substantially as indicated along the line 7—7 of FIG. 6;

FIG. 8 is a fragmentary elevational view of the sampling device and showing the device in a configuration permitting passage of a relatively large quantity of liquid through the device; and FIG. 9 is a view taken partly in section and being taken substantially as indicated along the line 9—9 of FIG. 8.

DESCRIPTION OF THE PREFERRED EMBODIMENTS

Referring now to FIG. 1, there is shown a liquid drainage bag generally designated 20 having a pair of opposed flexible side walls 22 and 24 defining a liquid collection chamber 26, a drip chamber 28 attached to the side wall 22 and communicating with the chamber 26, and a drainage tube 30 connected to the drip chamber 28 and communicating through the drip chamber with the collection chamber 26. During catheterization, a catheter (not shown) is located in the urethra of a patient with a distal end of the catheter located in the patient's bladder, and with a proximal end of the catheter located outside the patient's body and connected to a distal or upstream end of the drainage tube 30. In use, urine drains from the bladder through the catheter, drainage tube 30, and drip chamber 28 into the collection chamber 26 of the drainage bag 20 for retention therein. The drainage bag 20 also has a conduit 32 connected to the side wall 22 of the bag 20 and communicating with the collection chamber 26 at a lower portion of the chamber 26. As will be seen below, a liquid sampling device generally designated 34, which communicates with the conduit 32 may be used to obtain a urine sample or drain the collected urine from the chamber 26.

With reference to FIGS. 1-5, the liquid sampling device 34 comprises a tubular section 36 of flexible material, such as rubber, and a flow control element 38. As shown, the tubular section 36 has a cylindrical wall 40 having an inner surface 41 defining a lumen 42. The tubular section 36 also has a pair of opposed apertures 44 and 46 extending between the lumen 42 and the outside of the tubular section 36 in the region of enlarged portions 48 and 50 respectively surrounding the apertures 44 and 46.

The flow control element 38 comprises a spool member 52 having a pair of spaced circular discs 54 and 56 and a connecting portion 58 extending between the discs 54 and 56. As shown, the discs 54 and 56 are concentric and have approximately the same diameter, with the discs having a slightly greater diameter or width than the internal diameter of the tubular section lumen 42. The discs 54 and 56 have respective peripheral edges 60 and 62 which define separate surfaces for sealing against the inner surface 41 of the tubular section 36. Also, the spool member 52 has a thickness between outer side surfaces 64 of the discs 54 and 56 which is less than the internal diameter of the lumen 42. The connecting portion 58 of the spool member 52 is recessed from the peripheral edges 60 and 62 of the discs 54 and 56, respectively, such that the connecting portion 58 defines an annular groove 66 between the edges 60 and 62 of the discs 54 and 56. The connecting portion 58 of the spool member 52 also has a bore 68 extending through the connecting portion 58 along the rotational axis of the spool member during use.

The flow control element 38 also has an elongated stem 70 having a first cylindrical portion 72 adjacent one end 74 of the stem 70, a second cylindrical portion 76 spaced from the first portion 72 and located adjacent the other end 78 of the stem 70. The stem 70 also has an enlarged central portion 80 located intermediate the first and second portions 72 and 76, and having a size and shape to be snugly received in the bore 68 of the spool mmeber connecting portion 58. In the embodiment shown, both the stem central portion 80 and spool member bore 68 have a generally rectangular configuration. The stem 70 has an enlarged annular portion or rim 82 at the outer end 74 of the stem for a purpose which will be described below. The stem has an enlarged portion 84 adjacent the second stem portion 76 at the other end 78 of the stem 70. The flow control element 38 also has a handle member 86 connected to the other end 78 of the stem 70. In the embodiment shown, the handle member 86 comprises an enlarged flat extension of the stem 70.

The assembly of the sampling device 34 is described as follows. First, the spool member 52 is inserted into the lumen 42 of the tubular section 36, as shown in FIG. 3, with the spool member bore 68 being aligned with the opposed apertures 44 and 46. Next, the one end 74 of the stem 70 is inserted through the aperture 44 of the tubular section 36, through the bore 68 of the spool member 52, and through the opposed aperture 46 of the tubular section 36. In this configuration, as shown in FIG. 5, the first portion 72 of the stem 70 is located in the aperture 46 of the tubular section 36, and the second portion 76 of the stem 70 is located in the aperture 44 of the tubular section 36, thus permitting rotational movement of the stem in the tubular section apertures 44 and 46. Also, the central portion 80 of the stem is snugly received in the bore 68 of the spool member 52, and, since the stem central portion 80 and spool member bore 68 have similar shapes, rotational movement of the stem is imparted to the spool member 50 in the lumen 42. As shown in FIG. 5, the handle member 86 is located outside the tubular section 36, the enlarged portion 82 of the stem engages against an outer portion of the tubular section 36 adjacent the aperture 46, and the enlarged portion 84 of the stem engages against an outer surface 88 of the tubular section 36, such that the stem is retained for rotational movement in the apertures 44 and 46 of the tubular section 36.

With reference to FIGS. 3-5, the handle member 86 of the flow control element 38 may be utilized to place the spool member at a first rotational position with the discs 54 and 56 extending transversely across the lumen 42 of the tubular section. As shown, the elongated handle member is aligned with the discs, such that the orientation of the spool member in the lumen may be determined by the configuration of the handle outside the tubular section. In the first rotational position of the spool member, the peripheral edges 60 and 62 of the discs 54 and 56 engage against the inner surface 41 of the tubular section 36, and since the discs 54 and 56 are slightly larger than the lumen 42, the edges define sealing surfaces which sealingly engage against the inner surface 41 of the tubular section 36, such that the spool member prevents passage of liquid through the lumen 42. The device provides assurance that the control element prevents leakage in this configuration, since the spool member 52 has a pair of sealing discs. Thus, the spool member prevents passage of liquid through the tubular section at its first rotational position and in the normal configuration of the tubular section.

With reference to FIGS. 6 and 7, when a liquid sample is desired, the user may press opposed sides of the tubular section against the spool member 52 while the spool member is located at its first rotational position in the tubular section 36. As shown in FIG. 7, the application of such pressure against the flexible tubular section causes the tubular section wall 40 to deform slightly at opposed locations adjacent the first and second stem portions 72 and 76 and between the points where force is applied against the tubular section. As a result, the wall 40 becomes spaced slightly from the peripheral edges of the spool member discs, such that a relatively small quantity of liquid sample S passes between the spool member 52 and the inner surface 41 of the tubular section 36. In this manner, a specimen or sample may be readily obtained merely by squeezing the tubular section 36 between the fingers of one hand while a suitable receptacle may be held with the other hand to receive the sample at the outer end of the tubular section 36. After a sufficient quantity of the liquid sample has been collected in the receptacle, the tubular section may be released, and the tubular section wall 40 again assumes its sealing configuration against the spool member 52 in order to again close the lumen 42 and prevent passage of liquid through the tubular section.

When it is desired to drain liquid from the collection bag, the handle member 86 may be turned in either direction in order to rotate the spool member 52 into alignment with the lumen 42 at a second rotational position of the spool member, as shown in FIGS. 8 and 9. In this configuration, the spool member is located generally at a right angle relative the first rotational position, and the handle member is aligned with the longitudinal direction of the tubular section thus indicating the orientation of the spool member in the lumen. In the second rotational position of the spool member, at least portions of both disc peripheral edges 60 and 62 are spaced from the inner surface 41 of the tubular section, such that liquid freely passes around the outer side surfaces 64 of the spool member 52. Thus, the spool member 52 may be rotated to its second rotational position in the tubular section in order to drain liquid through the lumen 42.

When it is desired to again close the lumen 42 of the tubular section, the handle member 86 may be rotated approximately 90° in either direction such that the peripheral edges 60 and 62 of the spool member discs 54 and 56 sealingly engage against the inner surface 41 of the tubular section 36 at the first rotational position of the spool member, as previously described, in order to prevent passage of liquid through the tubular section. Thus, according to the present invention, a liquid sample may be readily obtained by merely squeezing the flexible wall of the tubular section, and liquid may be drained through the lumen by merely rotating the spool member in the tubular section.

With reference to FIG. 5, the first and second portions 72 and 76 of the stem 70 are constructed larger than the respective apertures 46 and 44 in which they are received, such that the first and second stem portions sealingly engage against the tubular section 36 in order to prevent leakage through the apertures 46 and 44. Also, as shown in FIGS. 4 and 5, the tubular section 36 has an inwardly directed boss 90 which projects into the lumen 42 and which is circumferentially aligned with the apertures 44 and 46 of the tubular section 36. When the spool member 52 is located at the first rotational position, the boss 90 is received in the annular groove 66 of the spool member 52 in order to releasably retain the spool member in its sealing configuration. When the spool member 52 is rotated through use of the handle member 86, the wall 40 of the tubular section 36 flexes slightly and the boss 90 snaps past one of the spool member discs, depending upon the direction of rotation of the spool member, after which the spool member may be rotated to its second rotational position in the lumen. When the spool member is rotated from the drainage position toward the first rotational position, the wall 40 of the tubular section 36 again flexes as one of the spool members discs passes the boss 90 which is again received in the annular groove of the spool member 52 in order to releasably retain the spool member at its sealing position.

The foregoing detailed description is given for clearness of understanding only, and no unnecessary limitations should be understood therefrom, as modifications will be obvious to those skilled in the art.

I claim:

1. A drainage bag, comprising:
 a receptacle having a pair of opposed walls defining a liquid collection chamber;
 a conduit connected to said receptacle and communicating with a lower portion of said chamber for draining liquid from the receptacle chamber, said conduit including a sampling section of flexible material having a wall defining a lumen and an outer surface adapted to be pressed by a user's fingers; and
 a flow control element comprising, a rigid valve member rotatably positioned in the lumen of said sampling section, said valve member having a width slightly greater than the internal dimensions of the surrounding sampling section and defining a peripheral surface for sealing against an internal surface of said wall, said valve member having a thickness less than the internal dimensions of the surrounding sampling section in at least one location, and said control element having a handle member located outside said tubular section and a stem extending through the wall of said sampling section and connecting said valve member and handle member, said valve member being located at a first rotational position in the sampling section with the peripheral surface of the valve member sealingly against the inner surface of the sampling section to close the lumen and prevent passage of liquid through the sampling section, the wall surface of said sampling section being pressed in the vicinity of the valve member with the valve member located at said first rotational position to deform the wall and permit a sample of the liquid to pass between the valve member and sampling section wall, and said valve member being rotated by said handle member to a second rotational position with at least a portion of said peripheral surface spaced from the inner surface of the sampling section to permit drainage of liquid between the valve member and the sampling section.

2. A liquid sampling device, comprising:
 a tubular section of flexible material having a wall defining a lumen for passage of liquid and an outer surface adapted to be pressed by a user's fingers, and at least one aperture extending between the lumen and the outside of the tubular section; and
 a flow control element comprising, at least one rigid disc rotatably positioned in said lumen, said disc having a greater external diameter than the internal diameter of said lumen and having a peripheral edge defining a surface for sealing against an inner surface of said tubular section, said disc having a thickness less than the internal diameter of said lumen, said control element having a stem connected to said disc and extending through the aperture of the tubular section to a location outside the tubular section, and a handle member connected to said stem outside the tubular section, said disc being located at a first rotational position with the sealing surface of said disc engaging against the inner surface of the tubular section to close the lumen and prevent passage of liquid through the tubular section, said tubular section surface being pressed in the vicinity of said disc to deform said wall and permit passage of a liquid sample between the disc and wall, and said disc being rotated by the handle member to a second rotational position with at least a portion of the disc edge spaced from the inner surface of the tubular section to permit passage of liquid between the disc and tubular section.

3. The device of claim 1 wherein the wall of said tubular section includes a second opposed aperture, and in which said stem extends through said second aperture.

4. A liquid sampling device, comprising:
 a tubular section of flexible material having a wall defining a lumen for passage of liquid and defining an outer surface adapted to be pressed by a user's fingers, and at least one aperture extending between the lumen and the outside of the tubular section; and a flow control element comprising, a spool member rotatably positioned in said lumen and having a pair of spaced concentric discs and a central portion connecting the discs with said discs being generally aligned, each of said discs having a greater external diameter than the internal diameter of said lumen and having a peripheral edge defining a surface for sealing against an inner surface of the tubular section, said spool member having a thickness less than the internal diameter of said lumen and an annular recess between said discs, said control member having a stem connected to the central portion of said spool member and extending through the aperture of the tubular section to a location outside the tubular section, and a handle member connected to said stem outside the tubular section, said spool member being located at a first rotational position with the sealing surfaces of both discs engaging against the inner surface of the tubular section to close the lumen and prevent passage of liquid through the tubular section, said tubular section surface being pressed in the vicinity of said spool member to deform said wall and permit passage of a liquid sample between the spool member and wall, and said spool member being rotated by the handle member to a second rotational position with at least a portion of the edges of both discs spaced from the inner surface of the tubular section to permit passage of liquid between the spool member and tubular section.

5. The device of claim 4 wherein the wall of said tubular section includes a second opposed aperture, and in which said stem extends through said second aperture.

6. The device of claim 4 wherein said tubular section includes an internal boss projecting into said lumen and generally aligned circumferentially around the lumen relative said aperture, said boss being received in the spool member recess with the spool member located at said first rotational position.

7. A liquid sampling device, comprising:
a tubular section of flexible material having a wall defining a lumen for passage of liquid and defining an outer surface adapted to be pressed by a user's fingers, and a pair of opposed apertures extending between the lumen and the outside of the tubular section; and a flow control element comprising, a spool member positioned in said lumen for rotation about an axis, said spool member having a pair of spaced circular discs and a connecting portion extending between the discs, said discs being concentric and having a substantially identical diameter, with said discs having a slightly greater diameter than the internal diameter of said lumen and having peripheral edges defining respective surfaces for sealing against an inner surface of the tubular section, said spool member having a thickness between outer side surfaces of said discs less than the internal diameter of said lumen, said connecting portion being recessed from the peripheral edges of said discs and defining an annular groove between the discs, and said connecting portion having a bore extending through the connecting portion along the rotational axis, said control member having an elongated stem having a first portion adjacent one end of the stem and received in one of said wall apertures, a second portion spaced from said first portion adjacent the other end of the stem and received in the other of said wall apertures, with said first and second stem portions being slightly larger than the respective wall apertures, and said stem having an enlarged central portion intermediate said first and second stem portions, said central stem portion being snugly received in the connecting portion bore of the spool member to impart rotational movement of the stem to the spool member, and said control element having a handle member extending from the other end of the stem outside the tubular section, said spool member being located at a first rotational position with the sealing surfaces of the discs engaged against the inner surface of the tubular section to close the lumen and prevent passage of liquid through the tubular section, said tubular section surface being pressed in the vicinity of the spool member to deform said wall and permit passage of a liquid sample between the spool member and wall, and said spool member being rotated about the rotational axis by the handle member to a second rotational position generally at a right angle relative the first rotational position with at least a portion of the edges of both discs being spaced from the inner surface of the tubular section to permit passage of liquid between the spool member and tubular section.

8. The device of claim 7 wherein said tubular section includes an internal boss projecting into said lumen and generally aligned circumferentially around the lumen relative said apertures, said boss being received in the spool member groove with the spool member located at said first rotational position.

9. The device of claim 7 wherein said tubular section includes enlarged portions adjacent said apertures.

10. The device of claim 7 wherein said bore of the spool member connecting portion and the central stem portion are generally rectangular.

11. The device of claim 7 wherein said stem includes an enlarged portion intermediate said first portion and the one stem end to retain the stem in place in the tubular section.

12. The device of claim 7 wherein said stem includes an enlarged portion intermediate said second stem portion and the handle member for engaging against an outer surface of the tubular section.

13. A liquid sampling device comprising:
a tubular section of flexible material having a wall defining a lumen for passage of liquid and defining an outer surface adapted to be pressed by a user's fingers;

a flow control element comprising, a generally circular rigid disc positioned in said lumen, said disc having a larger diameter than the internal diameter of said lumen, said disc having a peripheral edge sealingly engaging against an inner surface of the tubular section at a first angular position of the disc, said tubular section surface being pressed from opposed sides in the vicinity of the disc to deform said wall and permit passage of a liquid sample between the disc and the inner surface of the wall; and means for rotating said disc to a second angular position with at least a portion of said disc edge spaced from the inner surface of the tubular section to permit rapid passage of liquid through the control element.

* * * * *